Figure 1:
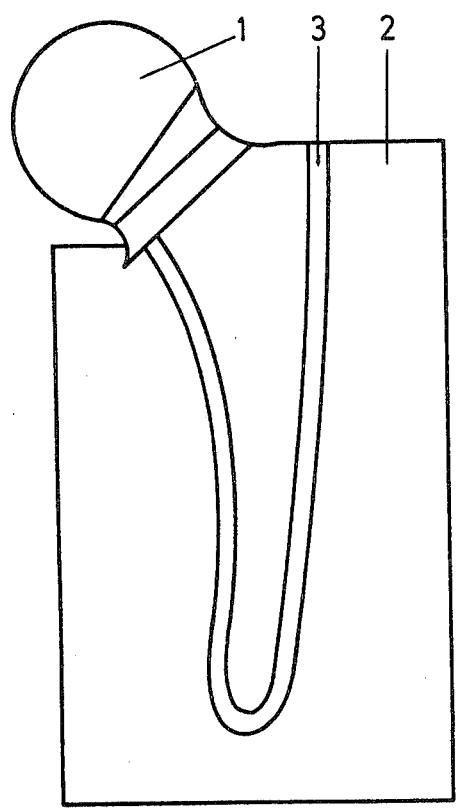

United States Patent [19]

Reiner et al.

[11] 4,202,055
[45] May 13, 1980

[54] ANCHORAGE FOR HIGHLY STRESSED ENDOPROSTHESES

[75] Inventors: Roland Reiner, Eschborn; Helmut Heide, Schwalbach; Karl Koster, Lorsbach, all of Fed. Rep. of Germany

[73] Assignee: Battelle-Institut e.V., Frankfurt am Main, Fed. Rep. of Germany

[21] Appl. No.: 796,164

[22] Filed: May 12, 1977

[30] Foreign Application Priority Data

May 12, 1976 [DE] Fed. Rep. of Germany ....... 2620907

[51] Int. Cl.² .............................................. A61F 1/24
[52] U.S. Cl. .................................... 3/1.91; 3/1.913; 128/92 CA; 433/201
[58] Field of Search ................... 3/1.9–1.913; 128/92 C, 92 CA, 92 G; 32/10 A

[56] References Cited

U.S. PATENT DOCUMENTS

| | | | |
|---|---|---|---|
| 3,787,900 | 1/1974 | McGee | 3/1.9 |
| 3,790,507 | 2/1974 | Hodosh | 3/1.9 X |
| 3,808,606 | 5/1974 | Tronzo | 32/10 A X |
| 3,918,100 | 11/1975 | Shaw et al. | 3/1.9 |
| 4,051,598 | 10/1977 | Sneer | 128/92 C |

Primary Examiner—Ronald L. Frinks
Attorney, Agent, or Firm—Fisher, Christen & Sabol

[57] ABSTRACT

An implantable prosthesis anchorage which contains a non-porous outer coating in the regions which is positioned in contact with bone. The non-porous outer coating consists of (i) at least one bioactive resorbable ceramic material which is a calcium phosphate and (ii) at least one polymer which is mechanically and chemically stable in the body. The ceramic material is in particulate form having particle diameters between 0.5 and 1 mm. The ceramic material particles is incorporated in the polymer in such a way that resorption of the ceramic material leads to a polymer structure with continuous pores filled with living bone tissue. Bioactivating bonding residues of the ceramic material are left on the inner surfaces of the filled pores which were created by the resorption of the ceramic material.

9 Claims, 7 Drawing Figures

ANCHORAGE FOR HIGHLY STRESSED ENDOPROSTHESES

BACKGROUND OF THIS INVENTION

1. Field of this Invention

The invention relates to an implantable prosthesis anchorage which consists of bioactive, resorbable ceramic materials on the basis of calcium phosphates and of polymers which are mechanically and chemically stable in the body. In addition, the invention relates to the production of the respective composite material, i.e., a system or a composite of materials for the cementless anchoring of highly stressed endoprostheses, especially joint endoprostheses or dental roots.

2. Prior Art

Anchoring of the predominantly metallic prostheses usual today is in general effected by means of a bone cement curing in situ, which mechanically anchors the shaft of the prosthesis in the "implant bed", i.e., an appropriate cavity made in the bone. This method is regarded as problematic today because the polymerising cement constituents release monomeric components to the surrounding tissue and thus initiates detrimental side reactions in the organism. In addition, the heat of reaction generated during polymerisation may cause destruction of the tissue. These and other reasons may lead to loosening of the prosthesis. The above disadvantages have given rise to various research activities aimed at developing cementless anchoring systems.

The improved tissue compatibility of highly stable oxide-ceramic prosthesis materials had suggested that these materials would be suitable for achieving direct bone-ceramic attachment (ingrowth of bone into the ceramic) and thus permit cementless achoring. Special surface structures of the prosthesis shaft characterised by grooves, cavities or the like were to foster the process of of mechanical anchoring. Unfortunately it has become obvious that this type of anchoring is not suitable for prostheses subject to high mechanical loads, e.g., the hip joint, where shear stresses occur at the implant bed; this is due to the fact that formation of a fibrous intermediate layer and atrophy of the bone finally lead to loosening of the prosthesis.

This finding has given rise to the use of so-called bioactive materials, which are to bring about direct contact between bone and materials surface without an intermediate fibrous boundary layer. These materials include, for example, calcium phosphates of specific compositions which ensure direct bone-prosthesis attachment without the formation of an intermediate fibrous boundary layer (cf. literature references: "Resorbierbare keramische Werkstoffe für den Knochenersatz", Biomedizinische Technik, vol. 20, May 1975, p. 115 ff; "Neuere Werkstoffe in der medizinischen Technik," Chemie-Ingenieur-Technik, No. 8, 1975, pp. 327–333). In specific structural composition and phase structure, these calcium phosphates are degradable in a biological environment, i.e., they are resorbed by the cells participating in the bone transformation. Although this material property is desirable in specific cases, it nevertheless precludes the use of calcium phosphates as the sole material for permanently implanted prostheses.

DESCRIPTION OF THE INVENTION

It is the objective of the present invention to create an anchorage suitable for functionally loaded endoprostheses, which ensures permanent contact between prosthesis and tissue.

It has been found that this objective can be achieved by a prosthesis anchorage of the above-described type which, according to the invention, consists of a nonporous outer coating on the prosthesis shaft with a polymer into which ceramic materials in particulate form have been incorporated such that upon resorption of the ceramic component a polymer structure with continuous pores is formed, and bioactivating residues of the ceramic being left on the inner pore surfaces. With the prosthesis anchorage according to the invention, bone tissue that has been newly formed after implantation can penetrate into the porous polymer structure simultaneous with pore formation or resorption of the ceramic.

According to an advantageous embodiment of the invention, the ceramic materials consist of sintered calcium phosphate particles of the chemical composition $CaO:P_2O_5$ at a molar ratio of about 3:1.

When preparing the prosthesis anchorage or rather the corresponding composite material according to the invention, the ceramic particles are in one embodiment of the invention charged on the surface, by chemical treatment prior to their incorporation in the polymer, with molecules with an affinity for polymers which bring about a firm chemical bond of calcium phosphates to the polymer within the region of the ceramic/plastic interfaces. Suitable molecules that have an affinity for polymers include acrylate-, methacrylate or vinyl-substituted di- or tri-halogen, -alkoxy or -acyloxy silanes which copolymerise with the polymer. In addition, silanes with at least one substituent readily soluble in the polymer and with 6 to 20 carbon atoms, where the polymer-affine molecule does not form covalent bonds with the polymer component but is connected with the latter by chemical bonds of the second order were also found to be suitable polymer-affine molecules. Advantageous polymers which have a sufficient mechanical stability include polyacrylates, polymethacrylates, polyacrylonitrile or their copolymers, or polyesters, polyamides, polyethylene terephtalate, high-density polyethylene, polypropylene, polysulphones, polyphenylene oxides, or the like.

The firm chemical bond of ceramic residues at the interface between ceramic and polymer or rather at the inner pore surface of the polymer structure has the result that during resorption of the ceramic particles in the border zone structural calcium phosphate groups are left in the polymer structure which serve as bioactivating bonding agents between the polymer and the tissue growing into it.

The invention is thus based on the finding that the solution of the problems under consideration requires combination of the resorbable bioactive calcium phosphates with a biostable polymer which has properties chemically and mechanically adapted to the bone; by interaction with calcium phosphates, these bio-inert polymers, which with their tissue compatibility to bones are "neutral" but not "bioactive", obtain the necessary bioactivity which finally leads to accelerated, direct ingrowth into the bone without an intermediate fibrous boundary layer.

In the composite according to the invention, the calcium phosphates are incorporated in the polymer—prior to implantation—in such a way that resorption of the ceramic results in a polymer structure with continuous pores, into which the newly formed bone tissue grows simultaneous with the resorption process.

In the production of the ceramic-polymer care has to be taken that the calcium phosphate particles are in contact with their neighbouring particles and that, nevertheless, enough free space remains in between which can be filled with the polymer. Optimum conditions exist if the calcium phosphate particles are of equal size and spherical. The wedge-shaped cavities in such a sphere packing would then remain for the polymer component.

To ensure that the porous polymer structure formed by resorption of the ceramic is and remains bioactive, so that direct contact with the bone is achieved, the pore surface of the polymer must contain bioactive molecules which are compatible with the bone tissue. The polymers which are suitable for the present application are not bioactive in themselves. In a preferred embodiment of the invention, the phosphate particles are therefore —prior to their incorporation in the polymer—subjected to the surface treatment briefly discussed in the foregoing and described in greater detail below, which gives them an affinity for the polymer:

The calcium phosphate is treated with silane derivates which form chemical compounds both with the calcium phosphate and among each other and have an additional functional group which leads to a firm bond to the polymer structure. A number of such silane derivates of the general formula $(Y-R-)_n Si-X_{4-n}$ are known, where "n" may have the value 1 or 2, "X" means a halogen alkoxy or acyloxy, and "Y" symbolises a group preferably covalently bound to the polymer. In the case of the polymers and copolymers from acrylates, methacrylates or acrylonitrile, "Y" is a vinyl group that copolymerises with these monomers.

By this process the calcium phosphate molecules close to the interface are bound so firmly that a calcium phosphate boundary layer is left in situ after resorption of the principal amount of the calcium phosphate constituent and thus a bioactive prosthesis surface results which produces bone-prosthesis attachment.

Further characteristic features, benefits and potential applications of the invention can be gathered from the following detailed description of specific examples for the preparation of the prosthesis anchorage according to the invention, including the pretreatment of the ceramic particles, on the basis of several drawings.

Figure 2:
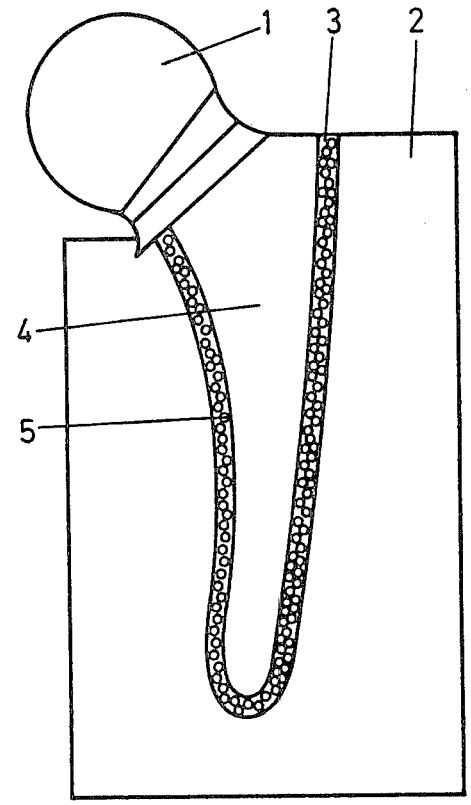
Figure 3:
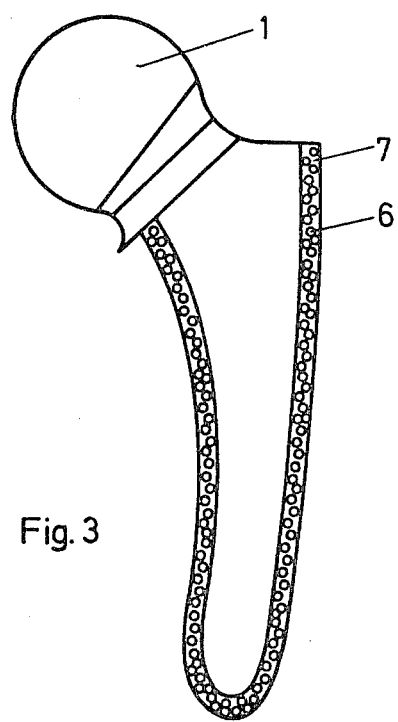
Figure 4:
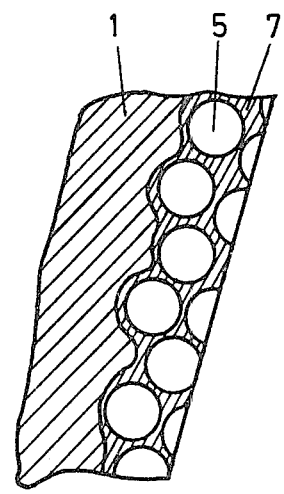

In the drawings:

FIGS. 1 to 3 are schematic drawings of a hip joint prosthesis during application of the non-porous outer coating on the prosthesis shaft according to the invention;

FIG. 4 shows an enlarged section of the border zone between prosthesis and non-porous outer coating according to FIG. 3, and FIGS. 5 to 7 show enlarged sections of various stages of ingrowth of newly formed bone into the prosthesis anchorage applied in the form of a non-porous outer coating according to the invention According to FIG. 1, a hip joint prosthesis 1 which consists of metal or oxide ceramic is first fixed in an appropriate mould 2 made, for example, of silicone rubber in such a way that a gap 3 of uniform width of about 2 to 3 mm is left between the prosthesis shaft and the wall of the mould. The width of this gap determines the later thickness of the non-porous outer coating on the prosthesis shaft.

Subsequently, this gap 3 is filled with spherical calcium phosphate particles 5 with diameters between 0.5 and 1 mm, as shown in FIG. 2. Then the gap 3 containing the spherical particles is filled with liquid monomers or a solution of polymers and monomers mixed with initiators, which are then polymerised. In the present case a 20-percent solution of polymethacrylate in monomeric methacrylate was used, to which 0.1 percent benzol peroxide an 0.2 percent para-toluidine had been added.

If thermoplastic polymers, in particular polyethylene, polyphenylene oxide or polypropylene, are used, the gap is filled with calcium phosphate particles and polymer powder, and the coating is produced by melting the polymer. A particularly suitable method for this is heating with simultaneous isostatic pressing, which is readily feasible with the above rubber mould.

In another embodiment of the invention, only the mould is covered with a dense layer of calcium phosphate particles, e.g. by lining the mould with an adhesive and then covering it with particles. The shaft of the prosthesis is then inserted in the gap and coated by polymerisation or embedding in polymers as before. Thus, a thinner, approximately "single-layer" coating (two-dimensional sphere packing) is obtained on the surface of the prosthesis.

Subsequently, the prosthesis 1 is removed from the mould (cf. FIG. 3); it is now covered with a polymer coating 7 with incorporated calcium phosphate particles 5. The shaft is then machined to expose the outer layer of the calcium phosphate particles. To achieve mechanical interlock between the prosthesis and the non-porous outer coating, the shaft of the prosthesis had been provided with a wavy or toothed surface structure, as is shown in FIG. 4; in addition to or instead of the surface asperities, it is possible to apply a bonding agent between the surface of the prosthesis and the polymer coating.

In many cases it is favourable to pretreat the calcium phosphate particles as follows:

A homogeneous powder mixture of two parts CaHPO$_4$ (calcium hydrogen phosphate) and one part CaCO$_3$ (calcium carbonate) is compressed and sintered in a kiln for two hours at a temperature of 1500° C. According to the formula

$$2CaHPO_4 + CaCO_3 \rightarrow 3CaO.P_2O_5 + H_2O \uparrow + Co_2 \uparrow$$

this reaction results mainly in tricalcium phosphate. As a structure analysis and an X-ray diffraction analysis have shown, the sintered product consists of a mixture of vitreous calcium phosphate with proportions of the α (high-temperature) and β (low-temperature) forms of tricalcium phosphate. The sintered product has a bulk density of 2.47 p/cm$^3$, i.e. it has only about 79 percent of the theoretical density. The residual porosity and the above phase composition have proved to be most advantageous for tissue compatibility and resorbability. To produce spherical particles these sintered products were pregranulated, ground plain in a rotating drum mill and finally screened.

Prior to incorporation in the polymer, the calcium phosphate particles are treated with commercial silanes carrying methacrylate groups. Thus it is possible to achieve on the Ca$_3$(PO$_4$)$_2$ surface a methacrylate substitution at a density of about 3μ mole silane substituents per gramme of Ca phosphate.

Figure 5:
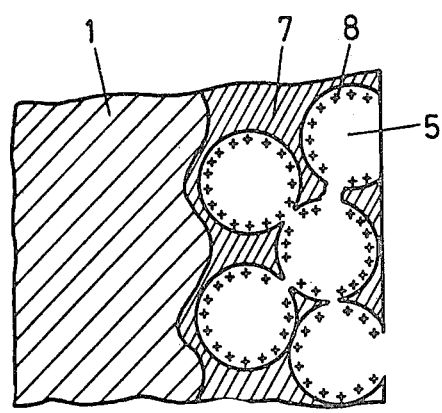

The individual processes involved in the application of the prosthesis anchorage according to the invention and the ingrowth of bone tissue can be explained as follows on the basis of FIGS. 5 to 7:

The monomer-polymer mixture of methacrylate and polymethacrylate, from which the polymer structure 7 as shown in FIG. 5 is produced, polymerises in the voids of the packing of surface-treated calcium phosphate particles 5, and copolymerises at the interface 8 between ceramic and polymer with the silanes carrying methacrylate groups, which are symbolised in FIG. 5 by +.

Figure 6:
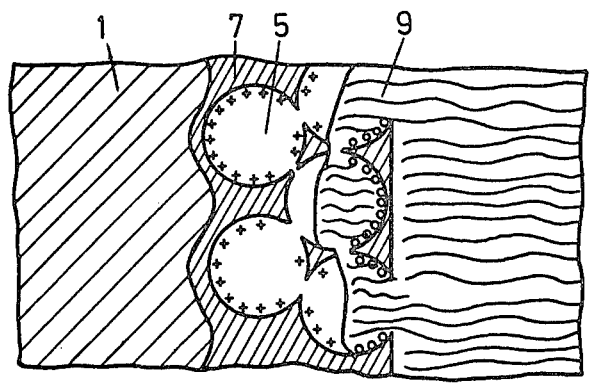

FIG. 6 illustrates the process of resorption of the calcium phosphate particles 5 and the simultaneous ingrowth of newly formed bone 9 into the polymer structure 7; during this process the bone 9 penetrates into the pore spaces from the outer surface of the anchorage formed by the prosthesis coating. Because of the chemical bond, residual calcium phosphate molecules 10 remain on the inside pore walls, thus forming a bioactivating border zone. These molecules 10 are symbolised in FIG. 6 by o.

Figure 7:
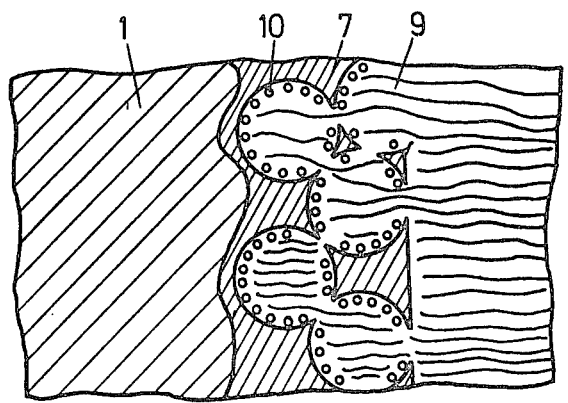

At the stage shown in FIG. 7, the process of ingrowth of the newly formed bone 9 into the residual porous polymer structure is finally completed. All the pores are filled with bone tissue; a composite region of high bearing strength has developed between the shaft of the prosthesis 1 and the bone 9.

What is claimed is:

1. An implantable prosthesis anchorage which contains a non-porous outer coating in the regions which will be positioned in contact with bone, the non-porous outer coating consisting of (i) at least one bioactive resorbable ceramic material which is a calcium phosphate and (ii) at least one polymer which is mechanically and chemically stable in the body, the ceramic material being in particulate form having particle diameters between 0.5 and 1 mm, and the ceramic material particles being incorporated in the polymer in such a way that resorption of the ceramic material leads to a polymer structure with continuous pores filled with living bone tissue, bioactivating bonding residues of the ceramic material being left on the inner surfaces of the filled pores which have been created by the resorption of the ceramic material.

2. A prosthesis anchorage as claimed in claim 1 wherein the ceramic material is sintered calcium phosphate particles having the chemical composition $CaO:P_2O_5$ at a molar ratio of about 3:1.

3. A prosthesis anchorage as claimed in claim 2 wherein the polymer is selected from the group consisting of a polyacrylate, a polymethacrylate, a polyacrylonitrile, a copolymer of polyacrylonitrile, a polyester, a polyamide, a high-density polyethylene, a polypropylene, a polysulphone and a polyphenylene oxide.

4. A prosthesis anchorage as claimed in claim 1 wherein the polymer is selected from the group consisting of a polyacrylate, a polymethylacrylate, a polyacrylonitrile, a copolymer of polyacrylonitrile, a polyester, a polyamide, a high-density polyethylene, a polypropylene, a polysulphone and a polyphenylene oxide.

5. An implantable prosthesis anchorage which contains a non-porous outer coating in the regions which will be positioned in contact with bone, the non-porous outer coating consisting of (i) at least one bioactive resorbable ceramic material which is a calcium phosphate and (ii) at least one polymer which is mechanically and chemically stable in the body, the ceramic material being in particulate form having particle diameters between 0.5 and 1 mm, the ceramic material particles being incorporated in the polymer in such a way that resorption of the ceramic material leads to a polymer structure with continuous pores filled with living bone tissue, bioactivating bonding residues of the ceramic material being left on the inner surfaces of the filled pores which have been created by the resorption of the ceramic material, and, prior to incorporation in the polymer, the ceramic particles have been charged on the surface with polymer-affine molecules which induced a firm chemical bond of the calciun phosphate to the polymer in the region of the ceramic/polymer interface.

6. A prosthesis anchorage as claimed in claim 5 wherein the polymer-affine molecules, which copolymerize with the polymer, are selected from the group consisting of a vinyl-substituted dihalogen silane, a vinyl-substituted trihalogen silane, a vinyl-substituted alkoxy silane, a vinyl-substituted acyloxy silane, an acrylate-substituted dihalogen silane, an acrylate-substituted trihalogen silane, an acrylate-substituted alkoxy silane, an acrylate-substituted acyloxy silane, a methacrylate-substituted dihalogen silate, a methacrylate-substituted trihalogen silane, a methacrylate-substituted alkoxy silane and a methacrylate-substituted acyloxy silane.

7. A prosthesis anchorage as claimed in claim 5 wherein the polymer-affine molecules are silanes with at least one substitutent which are readily soluble in the polymer and with 6 to 20 carbon atoms, and have been bound to the polymer component by chemical bonds of the second order rather than by covalent bonds.

8. A prosthesis anchorage as claimed in claim 5 wherein the polymer-affine molecules have the formula:

$$(Y-R-)_n SiX_{4-n}$$

wherein n is 1 or 2, X is halogen, alkoxy or acyloxy, and Y is vinyl, acrylate or methacrylate.

9. A prosthesis anchorage as claimed in claim 5 wherein the calcium phosphate particles are of equal size and are spherical and such individual particles are in contact with each other.

* * * * *